(12) United States Patent
Heath et al.

(10) Patent No.: US 7,340,324 B2
(45) Date of Patent: Mar. 4, 2008

(54) MIXING AND POURING APPARATUS AND VESSEL THEREFOR

(75) Inventors: Ellen M. Heath, Minnetonka, MN (US); Ruth Shuman, Minnetonka, MN (US); Douglas J. Kluge, Clearwater, MN (US); Glenn M. Campbell, Maple Grove, MN (US)

(73) Assignee: Qiagen North American Holdings, Inc., Germantown, MD (US)

( * ) Notice: Subject to any disclaimer, the term of this patent is extended or adjusted under 35 U.S.C. 154(b) by 921 days.

(21) Appl. No.: 10/687,449

(22) Filed: Oct. 16, 2003

(65) Prior Publication Data

US 2004/0092731 A1    May 13, 2004

Related U.S. Application Data

(63) Continuation of application No. 09/420,965, filed on Oct. 20, 1999, now abandoned.

(51) Int. Cl.
*G05B 21/00* (2006.01)
*G01N 21/00* (2006.01)

(52) U.S. Cl. .................. 700/266; 700/273; 702/19; 422/62; 422/63

(58) Field of Classification Search ............ 422/62–63, 422/67, 68.1; 700/266, 273; 702/19
See application file for complete search history.

(56) References Cited

U.S. PATENT DOCUMENTS

| | | |
|---|---|---|
| 3,189,072 A | 6/1965 | Starr |
| 3,622,279 A | 11/1971 | Moran |
| 3,858,740 A | 1/1975 | Lestaevel |
| 4,090,631 A | 5/1978 | Grussen |
| 4,175,860 A | 11/1979 | Bacus |
| 4,390,111 A | 6/1983 | Robbins et al. |
| 4,466,548 A | 8/1984 | Herbert |
| 4,632,808 A | 12/1986 | Yamamoto et al. |
| 4,712,220 A | 12/1987 | Luft |
| 4,846,361 A | 7/1989 | Haffner |
| 4,948,001 A | 8/1990 | Magly |
| 5,042,226 A | 8/1991 | Osip et al. |
| 5,104,621 A | 4/1992 | Pfost et al. |

(Continued)

FOREIGN PATENT DOCUMENTS

WO    WO95/28496    10/1995

(Continued)

OTHER PUBLICATIONS

Perbal, "A Practical Guide to Molecular Cloning," Copyright 1988, pp. 75, 305-307.

*Primary Examiner*—Brian R. Gordon
(74) *Attorney, Agent, or Firm*—Leffert Jay & Polglaze, P.A.

(57) ABSTRACT

A mixing and pouring apparatus for computer controlled processing of mixing and pouring operations includes a rotatable arm capable of holding vessels therein, the arm rotatable at programmable speeds and time lengths to perform automated moving and pouring processes. The present invention further provides a cap and vessel positioning system that securely locks a vessel in place and realigns the cap in essentially the identical position in relation to the vessel every time the vessel is capped. In one embodiment, both the cap and vessel have flanges that are aligned when the cap is properly secured to the vessel.

27 Claims, 13 Drawing Sheets

U.S. PATENT DOCUMENTS

| | | |
|---|---|---|
| 5,143,235 A | 9/1992 | Repp |
| 5,217,593 A | 6/1993 | MacConnell |
| 5,330,914 A | 7/1994 | Uhlen et al. |
| 5,369,566 A | 11/1994 | Pfost et al. |
| 5,384,096 A | 1/1995 | Burns |
| 5,389,339 A | 2/1995 | Petschek et al. |
| 5,458,854 A | 10/1995 | Burns |
| 5,473,855 A | 12/1995 | Hidding et al. |
| 5,584,039 A | 12/1996 | Johnson et al. |
| 5,679,154 A | 10/1997 | Kelley et al. |
| 5,687,552 A | 11/1997 | Barca |
| 5,692,144 A | 11/1997 | Thrush |
| 5,773,221 A | 6/1998 | Carlson et al. |
| 5,800,828 A | 9/1998 | Dionne et al. |
| 5,802,389 A | 9/1998 | McNutt |
| 5,856,133 A | 1/1999 | Stephens et al. |
| 5,863,801 A | 1/1999 | Southgate et al. |
| 5,918,442 A | 7/1999 | Dewees et al. |
| 5,922,320 A | 7/1999 | Vogel et al. |
| 5,946,220 A * | 8/1999 | Lemelson .................. 700/273 |
| 5,967,352 A | 10/1999 | Repp et al. |
| 6,006,930 A | 12/1999 | Dreyer et al. |
| 6,072,795 A | 6/2000 | Poulter |
| 6,102,224 A | 8/2000 | Sun et al. |
| 6,232,464 B1 | 5/2001 | Lange |
| 6,273,848 B1 | 8/2001 | Marziali |
| 7,024,281 B1 * | 4/2006 | Unno ........................ 700/275 |
| 7,099,721 B2 * | 8/2006 | Dunnill et al. ................ 700/73 |
| 7,159,740 B2 * | 1/2007 | Nanthakumar et al. ..... 221/224 |
| 2005/0118650 A1 * | 6/2005 | Dasseux et al. ............. 435/7.2 |
| 2005/0260743 A1 * | 11/2005 | Drake et al. ............. 435/289.1 |
| 2006/0228695 A1 * | 10/2006 | Mattheakis et al. ............ 435/4 |

FOREIGN PATENT DOCUMENTS

| | | |
|---|---|---|
| WO | WO99/13976 | 3/1999 |
| WO | WO 99/21658 | 5/1999 |
| WO | WO00/45164 | 8/2000 |

* cited by examiner

MIXING AND POURING APPARATUS AND VESSEL THEREFOR

CROSS REFERENCE TO RELATED CASES

This Application is a continuation of U.S. application Ser. No. 09/420,965 filed Oct. 20, 1999 now abandoned and also claims priority to U.S. application Ser. No. 09/255,146, entitled COMPUTER IMPLEMENTED DNA ISOLATION METHOD, filed Feb. 22, 1999 (pending), and Ser. No. 09/361,829, entitled COMPUTER IMPLEMENTED NUCLEIC ACID ISOLATION METHOD AND APPARATUS, filed Jul. 27, 1999 (pending) which were incorporated by reference in the parent application.

FIELD

The present invention relates generally to holding, mixing and pouring of vessels, and more particularly to mixing and pouring devices designed for vessels having removable screw caps, and the vessels themselves.

BACKGROUND

Currently, manual processes for working with chemicals in solution, isolation of components from solution, and the like involve time intensive operation of one (1) to 24 hours, including an overnight incubation period. Further, samples may need to be mixed, shaken, poured, agitated, and the like for certain time periods or a certain number of iterations.

In many lab processes, a sample of some material which contains components to be isolated, mixed, or the like is typically placed in a sample vessel, and processes comprising the steps to be performed on the sample are performed on the vessel and its contents. Materials may be removed from the vessel, added to the vessel, transferred to another vessel, and the like.

Typical lab procedures for working with samples include mixing and agitating the sample, adding material to the sample, removing material from the sample by pouring, and the like. These processes have traditionally been performed by hand. Such manual performance of tasks has been and continues to be labor intensive, requiring time consuming and repetitive tasks that occupy a technician, often to the exclusion of other tasks. The repetitive process steps of processes for working with chemicals, solutions, suspensions, and the like as described above require precision and attention to detail, and may often rely on the skill of the technician responsible for the isolation. Repetitive application of precise process steps lends itself to errors which may negatively affect the quality of the processes performed. In the case of unique or limited samples, such errors may occur when dealing with samples that cannot be duplicated, or are irreplaceable.

Further, during many types of laboratory procedures, such as isolation of DNA, vessels are capped and recapped so that samples and reagents can be added, contents can be shaken or moved, and so forth. Many manufacturing processes, including processes for producing packaged foods, chemicals, medicines, and so forth also involve capping or uncapping of vessels, and the adding and removal of contents.

Typically, threaded vessels and caps are used. Oftentimes, however, it is difficult to start the cap threads squarely on the vessel threads, which can cause the cap to not be securely attached, leading to leakage of vessel contents. In some cases, it may be necessary to stop the entire operation to clean up the spill, leading to reduced productivity. During precise laboratory procedures, such as DNA or RNA isolation, such content loss can also cause contamination and cross-contamination of samples and the laboratory, such that the entire process needs to be restarted. Furthermore, if the vessel itself rotates as the cap is being secured, the vessel may remain uncapped or the cap may not be in the proper position, again leading to problems with loss of vessel contents. Vessel movement can also adversely affect fragile contents, such as coagulated DNA strands suspended in a liquid, which can be torn by viscous effects in the liquid.

SUMMARY

The present invention overcomes the problems of the prior art by providing a mixing and pouring apparatus for performing mixing and pouring tasks without requiring a user to perform the tasks, and vessels for use in such an apparatus.

The present invention further overcomes the problems of the prior art by providing a cap and vessel positioning system that securely locks a vessel in place and realigns a cap in essentially the identical position in relation to the vessel every time the vessel is capped. In one embodiment, both the cap and vessel have flanges that are aligned when the cap is properly secured to the vessel.

In one embodiment, a mixing and pouring apparatus includes a base, and a locking arm support carried on the base. A locking arm is rotatably mounted within the locking arm support, and a drive mechanism is operatively coupled to the locking arm, the drive mechanism capable of rotating the locking arm.

In another embodiment, a vessel having a substantially square flange at the base of a series of external threads is disclosed. A cap having a substantially identical square flange and internal threads is threaded onto the vessel. In one embodiment, the vessel has multiple disjointed threads to provide an improved surface for starting the threads. In one embodiment, four-start threads are used. In this embodiment, the cap is adequately secured after minimal turning.

In another embodiment, the cap and positioning system further comprises a locking device for securing the vessel in a fixed position. The locking arm can be a pair of partitions on a lab rack, or a locking pocket in a storage rack or the shaking and pouring device as described above.

In another embodiment, a method for positioning and repositioning a vessel and cap in a substantially identical location is disclosed. The method further includes securing the vessel or a vessel and cap assembly in a suitable locking arm for storage, transport, shaking, and so forth.

Other embodiments are described and claimed.

DESCRIPTION OF EMBODIMENTS

Figure 1:
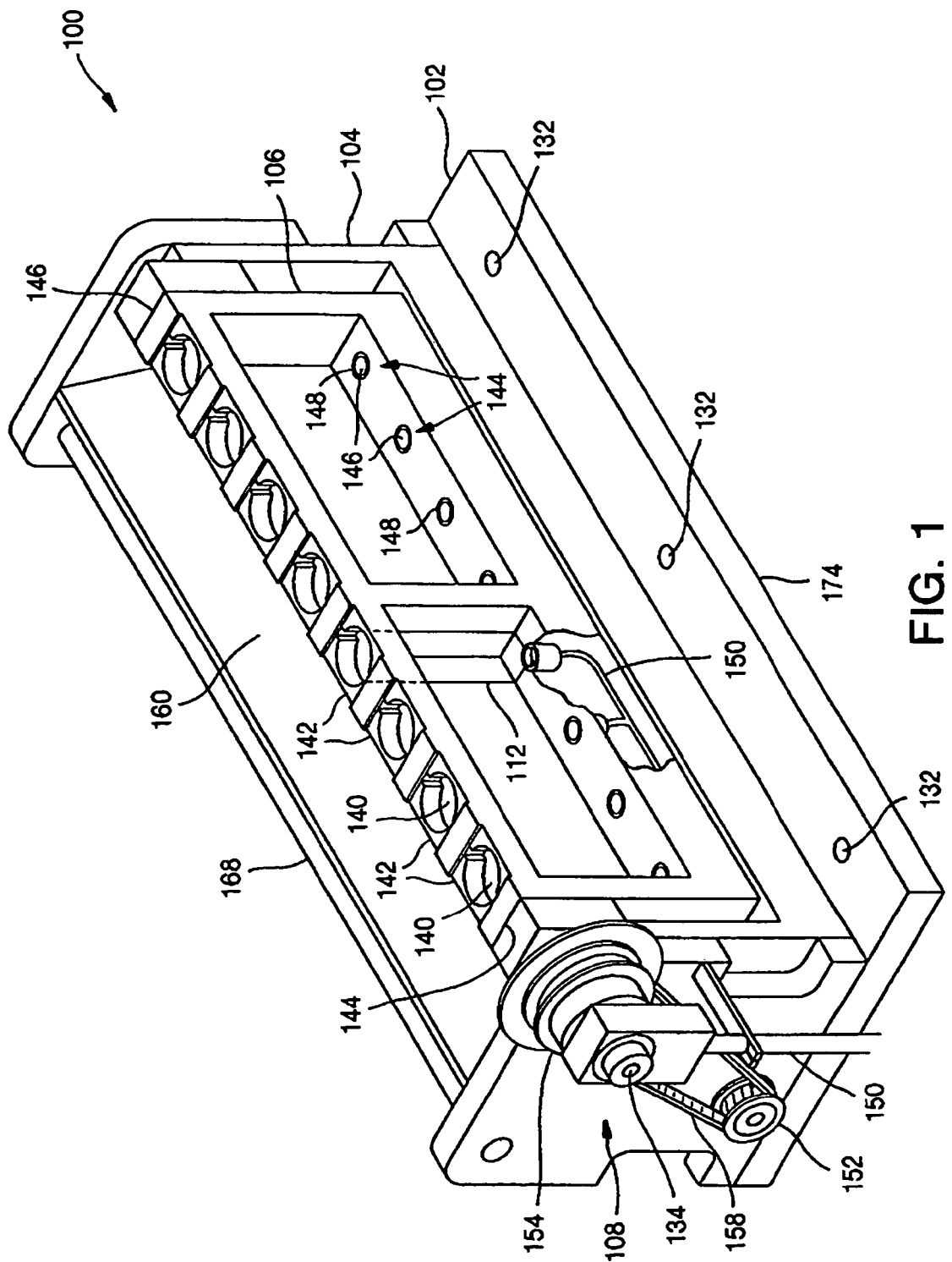
FIG. 1 is a perspective view of one embodiment of an apparatus for mixing and pouring.

In the following detailed description of embodiments, reference is made to the accompanying drawings which form a part hereof, and in which are shown by way of illustration specific embodiments in which the invention may be practiced. In the drawings, like numerals describe substantially similar components throughout the several views. These embodiments are described in sufficient detail to enable those skilled in the art to practice the invention, and it is to be understood that other embodiments may be utilized and logical, structural, electrical, and other changes may be made without departing from the scope of the present invention.

FIG. 1 shows one embodiment of a mixing and pouring apparatus 100. Mixing and pouring apparatus 100 comprises a base 102, a locking arm support 104, rotatable locking arm 106, drive mechanism 108, and motor 130 (shown best in FIG. 2). Mixing and pouring apparatus 100 is suitable for use with a vessel and cap structure 110 such as vessel 112 and cap 114 shown in greater detail in FIGS. 11, 11A, 12A, 12B, 12C, 13A, and 13B and described below.

Base 102 serves as a support for the remaining components of the mixing and pouring apparatus 100. Base 102 includes on one embodiment guide pin openings 132 capable of receiving a supplemental vessel and cap cradle for use in a pouring operation to be described later. Locking arm support 104 includes openings for receiving a support or supports for the locking arm 106 at its ends 144 and 146. Shaft 134 of locking arm support 104 is fixedly connected to drive mechanism 108 and locking arm 106 for effecting motion of locking arm 106 is response to operation of the drive mechanism 108.

Locking arm 106 is rotatable about the longitudinal axis of the shaft 134, and is rotated upon actuation of the drive mechanism 108 to effect the rotation or other motion of the locking arm 106 initiated by the drive mechanism 108. As will be described in greater detail below, locking arm 106 is capable of holding and retaining vessels such as vessel 112 within one of a plurality of vessel openings 140 in the top of the locking arm 106. As will be described below, each of the vessel openings 140 in the locking arm 106 is surrounded by a locking pocket 142 which is shaped and sized in one embodiment to match a flange such as flange 118 of a vessel such as vessel 112 to secure the vessel against rotation in the locking pocket 142 and opening 140.

Figure 16:
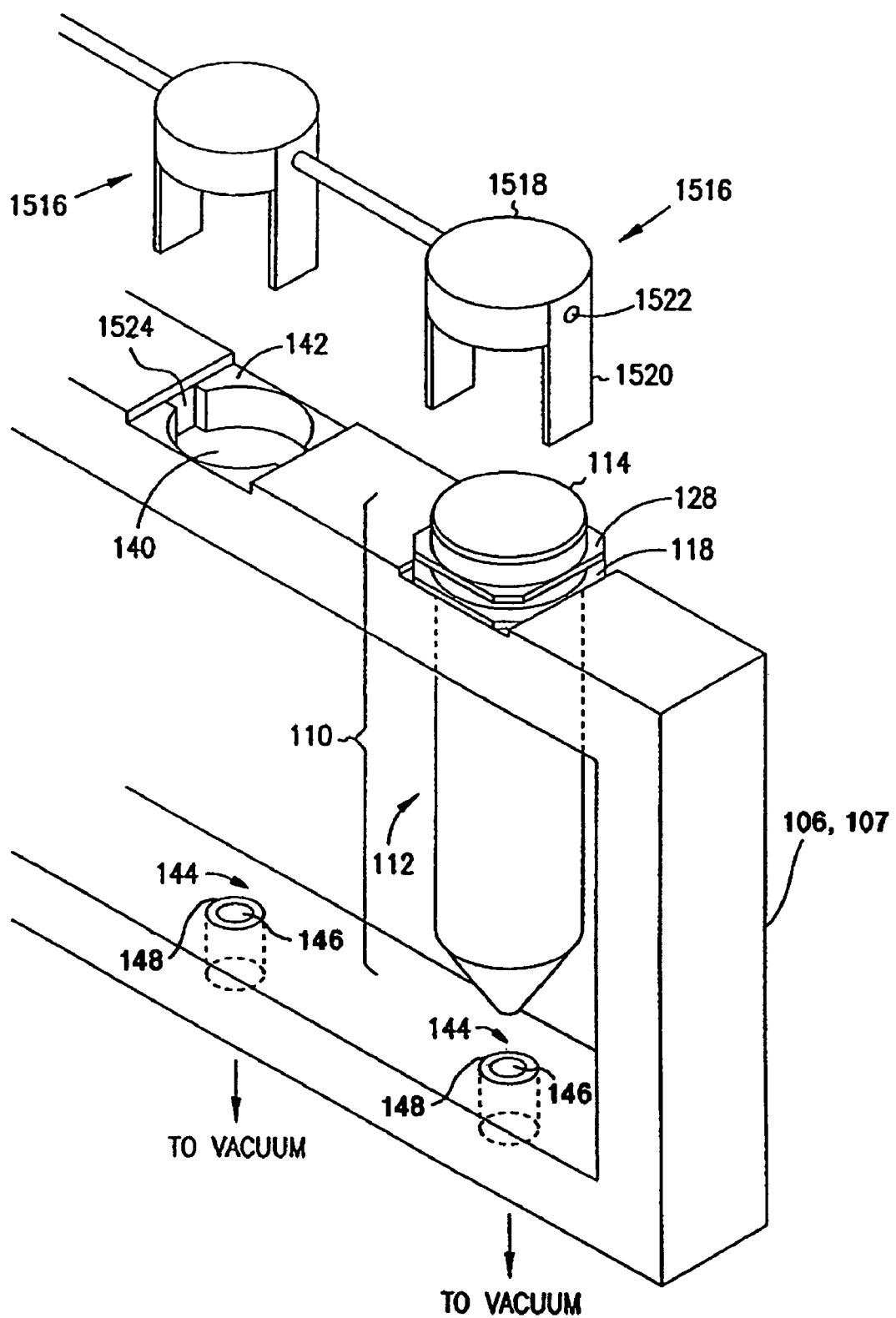
FIG. 16 is a cut-away perspective view of vessels with caps in a shaking and pouring device in one embodiment of the present invention.

The locking arm 106 further comprises in one embodiment vacuum locking ports 144 which serve to secure a vessel such as vessel 112 into the locking arm 106 so that the locking arm with the vessel therein may be rotated, tipped, inverted, or the like, without the vessel falling out of the locking arm. In this embodiment, each of the locking ports 144 comprises a locking opening 146 (also shown in FIG. 16) having at its edge an O-ring 148 to seal the opening 146 when a vessel such as vessel 112 is placed in the opening 146 and a vacuum or partial vacuum is drawn below the port 144.

A vacuum or partial vacuum is drawn below the port 144 which holds the vessel 112 against the O-ring 148 within the port opening 146, thereby retaining the vessel 112 within the port 144 and within the locking arm 106. Once the vessel 112 is secured within the port 144, the locking arm may be rotated, tipped, or the like without the vessel 112 being separated from the locking arm. If a cap such as cap 114 is on the vessel 112, then any motion of the locking arm 106 will result in an agitation, nixing, or shaking of the contents of the vessel 112. If the cap 114 is removed from the vessel 112, then the rotation of the locking arm 106 will result in a pouring of contents from the vessel 112.

In one embodiment, a vacuum line 150 is connected to an external vacuum pump in one embodiment. It should be understood that an internal vacuum pump could also be used. It is sufficient that some vacuum pump be connected to the ports 144 to draw a partial vacuum below the vessel tip 117. In cutaway in FIG. 1, one embodiment of a connection of a vacuum line 150 to several ports 144 is shown. In this embodiment, the vacuum line 150 is connected from an external vacuum pump to the locking arm 106. Internal to the locking arm, the vacuum line 150 is connected to each of the ports 144 so as to draw a partial vacuum at each port when the vacuum pump is turned on.

The partial vacuum is also applied when the contents of the vessel 112 are being poured out so that the vessel 112 will not fall out of the mixing and pouring station 100 as it is being tipped. In this way, the vessel 116 can be rotated beyond a horizontal position without slipping out, and its contents emptied out completely, or sufficiently to remove excess material while leaving desirable material in the vessel 112.

In other embodiments, other apparatuses for holding vessels such as vessel 112 within the locking arm 106 include by way of example only and not by way of limitation clamps, threads, clips, pins, and the like. It is sufficient that the vessels be held in the locking arm 112 so that if inverted, the vessels will not fall out of the locking arm 112.

Figure 2:
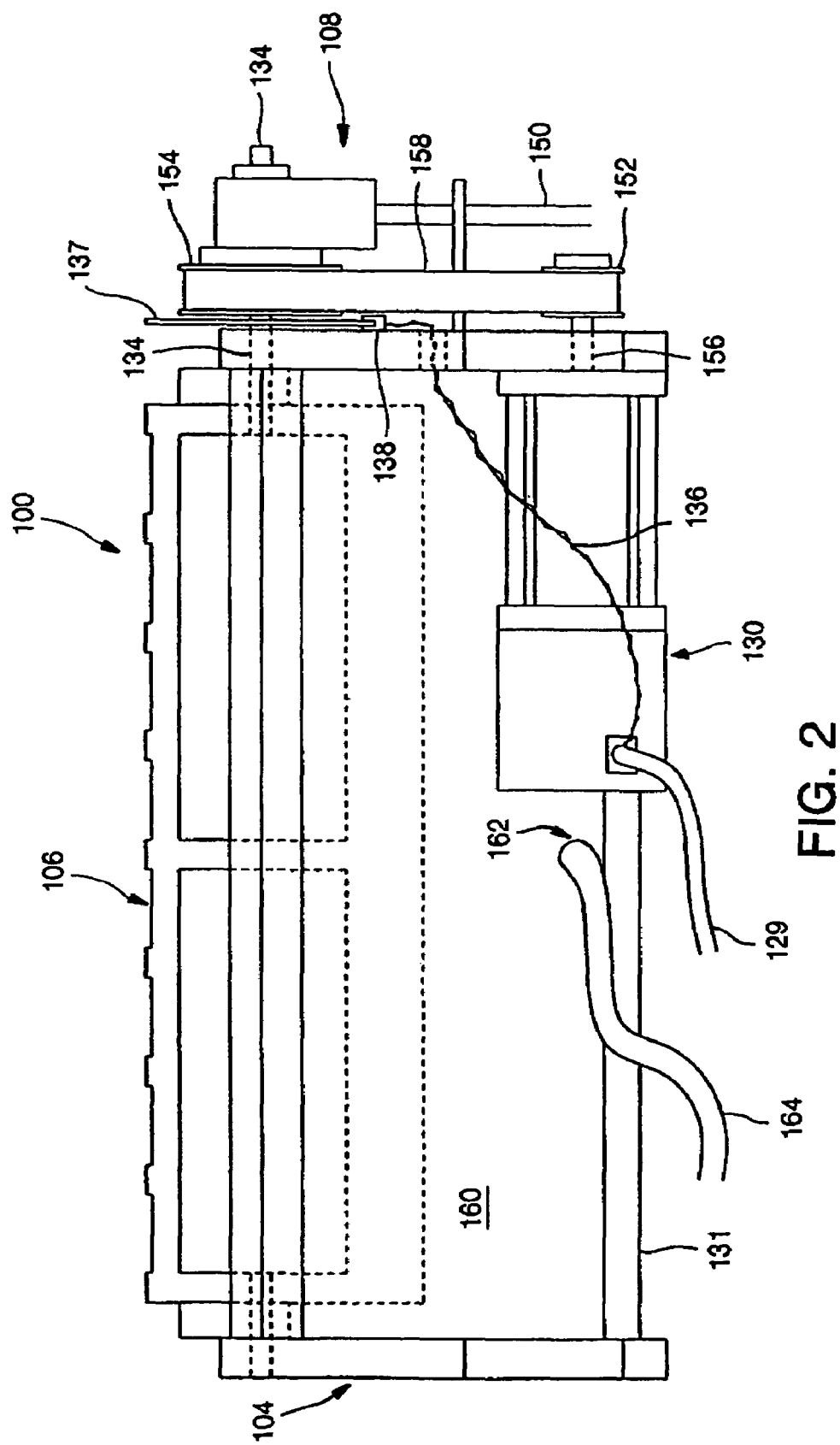
FIG. 2 is a rear elevation view of the embodiment of FIG. 1.

As is best seen in FIGS. 1 and 2, the drive mechanism 108 comprises in one embodiment a pair of gears, drive gear 152 and free gear 154. Drive gear 152 is operatively coupled to shaft 156 of motor mechanism 130, and therefore rotates when shaft 156 rotates. Free gear 154 is fixedly coupled to shaft 134, and rotates therewith. As has been mentioned, shaft 134 is fixedly coupled to locking arm 106. Therefore, when free gear 154 rotates, shaft 134 and locking arm 106 also rotate. A belt 158 is seated over gears 152 and 154. In one embodiment, gears 152 and 154 are notched, and belt 158 is notched, so that the notches of belt 158 fit the notches of gears 152 and 154. In this embodiment, rotation of the drive gear 152 directly corresponds to rotation of the free gear 154 at a known ratio. The notches of the gears 152 and 154, and of the belt 158, eliminate to a large extent any potential slippage of the belt 158 on the gears. When the motor 130 operates, the shaft 156 rotates, driving the drive gear 152, moving the belt 158 to rotate the free gear 154 and consequently the shaft 134 and the locking arm 106.

The motor 130 is in one embodiment controlled externally by a computer control. Computer control signals are sent to the motor 130 along line 129. Such a computer control allows the choice by a user of the operation of the motor, and therefore the motion of the locking arm through the operation of the drive mechanism 108. In this embodiment, a user can program a single operation of the locking arm, or multiple operations of the locking arm. For example, if it is desired to mix the contents of a vessel retained within the locking arm, the user may choose rotation of the locking arm in complete 360 degree rotations about the longitudinal axis of the shaft. The speed of rotation is adjusted or set by the user, and the known ratio of the drive gear size to the free gear size allows the computer to program the motor to drive shaft 156 at the appropriate rotational speed to supply the desired rotational speed of the locking arm 106.

Motor 130 is in one embodiment a so-called smart motor. The motor 130 in this embodiment includes a processor and memory (FIG. 9) which are capable of executing and storing a series of commands for operation of the apparatus 100 without further input from an external control. The commands are in one embodiment downloaded to the memory over computer control line 129, and are executed in the process without further input from the external computer control. In this embodiment, an entire sequence of steps may be programmed into the motor 130 for execution at a later time, such as when the apparatus 100 is unattended, or when the steps of the process are lengthy and it is not necessary for a user such as a scientist or technician to be present to oversee each step or the full process.

A computer control system capable of operating the apparatus 100 is disclosed in co-owned U.S. application Ser. No. 09/255,146, entitled COMPUTER IMPLEMENTED DNA ISOLATION METHOD, filed Feb. 22, 1999, and Ser. No. 09/361,829, entitled COMPUTER IMPLEMENTED NUCLEIC ACID ISOLATION METHOD AND APPARATUS, filed Jul. 27, 1999, which are herein incorporated by reference in their entirety.

Figure 6:
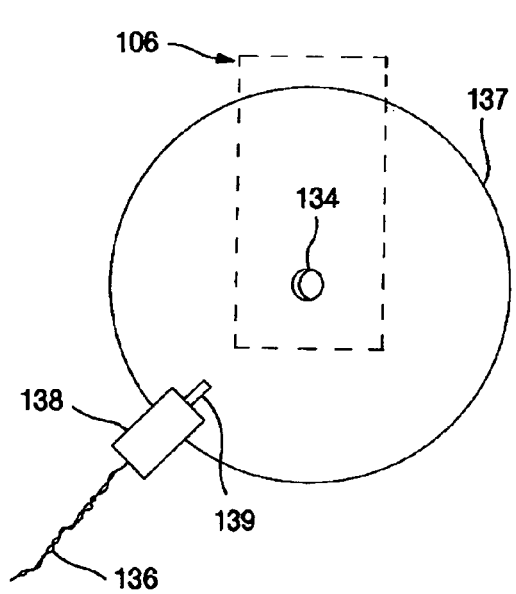
FIG. 6 is a front elevation view of an embodiment of a registration mechanism of the present invention in a home position.

Motor 130 and drive mechanism 108 in one embodiment have a registration mechanism to ensure that the locking arm begins its operational processes from the same position each time the apparatus 100 is started. Such registration mechanism is shown in greater detail in FIGS. 2, 6, and 7. A registration disk 137 is fixedly attached to shaft 134, so that registration disk 137 will rotate when shaft 134 rotates as described above. Registration disk 137 has therein along its circumference a registration slot 139 extending inward from the outer edge toward shaft 134. In the position shown in FIG. 6, the registration slot is aligned with optocoupler 138 when the locking arm 106 is substantially vertical with respect to the plane 131 of the base 102 of apparatus 100.

Optocoupler 138 has an optical transmitter 133 each electrically connected to the motor 130. Transmitter 133 emits a light signal. When slot 139 is between the transmitter 133 and optical receiver 135, receiver 135 receives the light signal from transmitter 133, indicating that the registration disk 137 is in its "home" position, that is, the locking arm 106 is substantially vertical with respect to plane 131. If no signal is received by receiver 135, then the registration disk 137 and hence the locking arm 106 and any vessels 112 retained therein are not substantially vertical. The motor 130, upon startup, will rotate the shaft 156, and therefore operated drive mechanism 108, to bring the registration disk 137 back to its home position before initiating any mixing or pouring operations.

Figure 7:
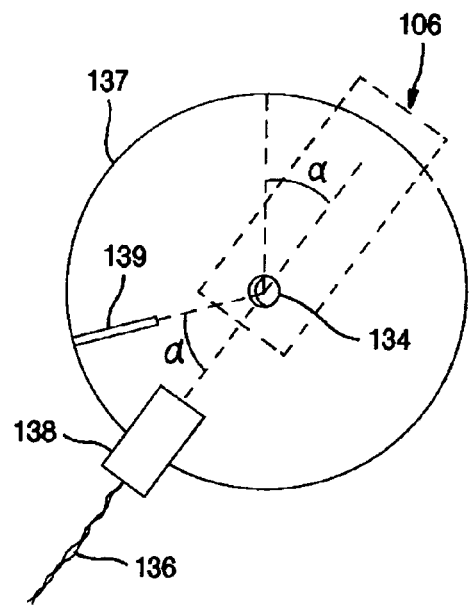
FIG. 7 is a front elevation view of the embodiment of FIG. 6 with the registration mechanism displaced from its home position.
Figure 8:
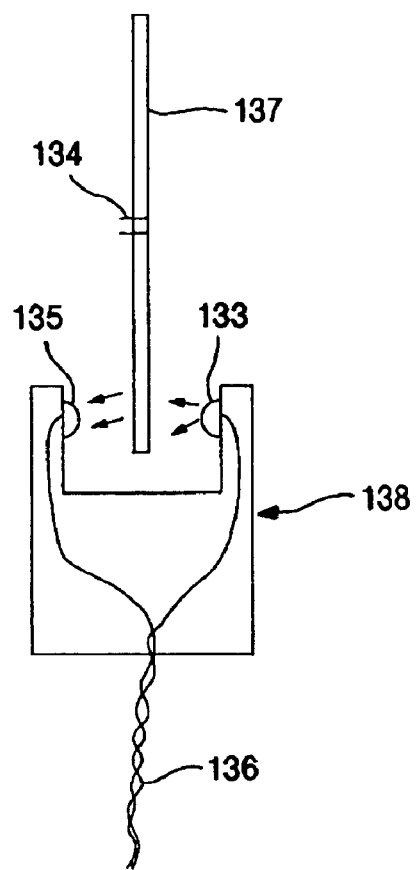
FIG. 8 is a side elevation view of the embodiment of FIG. 6.

In the position shown in FIG. 7, the registration disk 137 has rotated through an angle α, as has the locking arm 106. If the locking arm is rotated away from the home position shown in FIG. 6 before initiation of a process step, the optocoupler does not make a connection and the motor rotates the shaft 156 until the optocoupler makes a connection between its transmitter 133 and receiver 135.

It should be understood that other registration mechanisms may be used without departing from the scope of the invention. For example, but not by way of limitation, such registration could be accomplished by manual rotation and alignment, through the known gear ratio of free gear 154 to drive gear 152, or the like.

Alternatively, the user may choose to invert the vessels retained within the locking arm 106. This action may be repeated multiple times. It should be understood that any number of sequences of rotational motion may be programmed into a computer control as described above, or may be initiated by the user by utilizing the computer control.

Another action which may be desired by a user is a pouring action. In many laboratory processes, materials must be poured from the vessels. The material removed from the vessel may be waste material, or it may be material to be saved. Such pouring operations are referred to herein as "pour to waste" and "pour to save" respectively.

Figure 3:
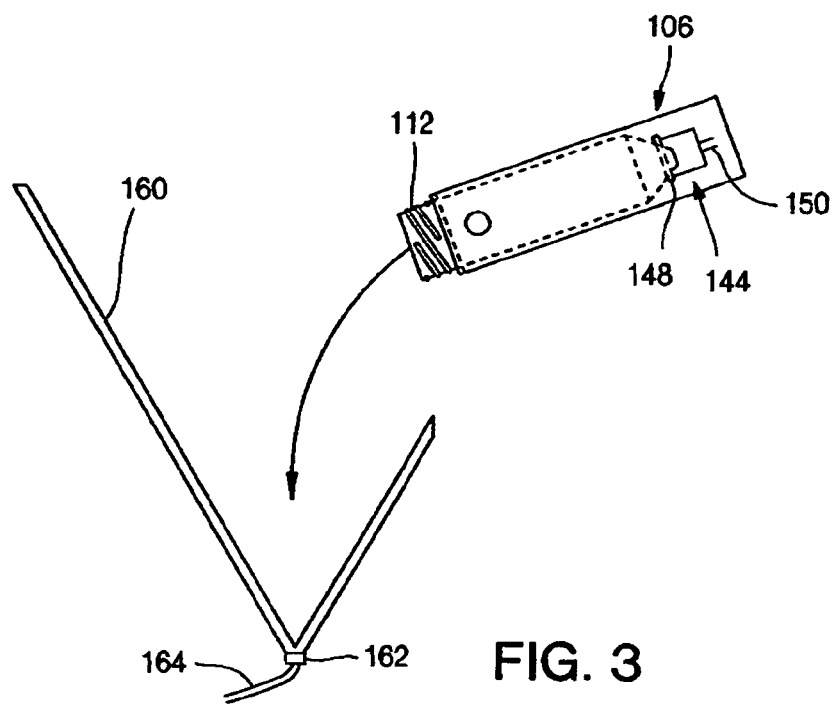
FIG. 3 is a partial side view of a trough embodiment of the present invention pouring to waste.
Figure 5:
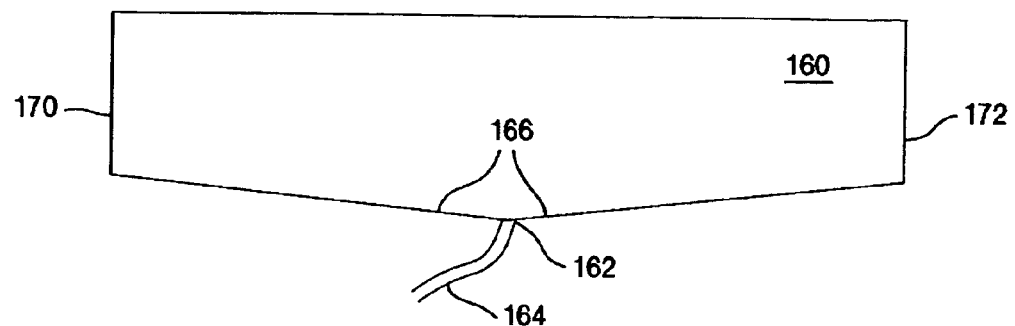
FIG. 5 is a front elevation view of a trough embodiment of the present invention.

The locking arm support 104 of apparatus 100 in one embodiment includes a waste trough 160 (FIGS. 1, 3, and 5) having a center drain 162 connected to a drain hose 164. Waste trough 160 receives "pour to waste" material poured from a vessel 112 retained within the locking arm 106 when the vessel 112 has its cap 114 removed and the locking arm 106 rotates toward the back 168 of apparatus 100. As is best seen in FIG. 3, when locking arm 106 is rotated toward back 168 of apparatus 100 while a capless vessel 112 is retained within locking arm 106, any waste fluid from vessel 112 is poured into trough 160 to drain out drain 162 and drain hose 164.

In one embodiment, trough 160 has bottom surfaces 166 which are angled downward and inward from edges 170 and 172 of trough 160 so that drain 162 is located at the physical lowest point of trough 160 when trough 160 is substantially vertical, to facilitate proper draining of waste material from trough 160. It should be understood that any drain configuration allowing the trough 160 to drain would suffice, and the invention is not limited to a center drain.

Figure 4:
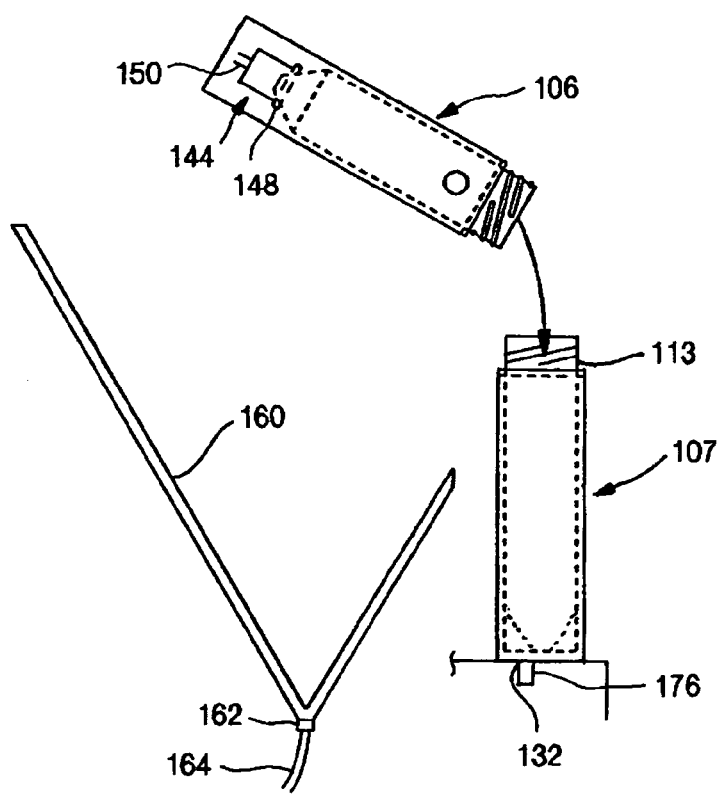
FIG. 4 is a partial side view of the trough embodiment of FIG. 3 pouring to save.

Referring now also to FIG. 4, one embodiment of a pour to save configuration is shown in greater detail. In the pour to save operation, when a capless vessel 112 is retained within locking arm 106, and locking arm 106 is rotated toward the front 174 of apparatus 100, any fluid from the vessel 112 is poured from the vessel 112 into another vessel 113 held in a supplemental vessel cradle 107 which is similar in shape and size to locking arm 106, but which does not contain the vacuum ports or vacuum connections of locking arm 106. Cradle 107 has a plurality of guide pins 176 which engage guide pin openings 132 in base 102 of apparatus 100 so as to position supplemental cradle 107 to receive vessels such as vessel 113 capable of retaining fluid poured from vessels 112 retained within locking arm 106.

As they are used herein, the terminology top, bottom, and sides are referenced according to the views presented. It should be understood, however, that the terms are used only for purposes of description, and are not intended to be used as limitations. Orientation may change without departing from the scope of the invention.

Figure 9:
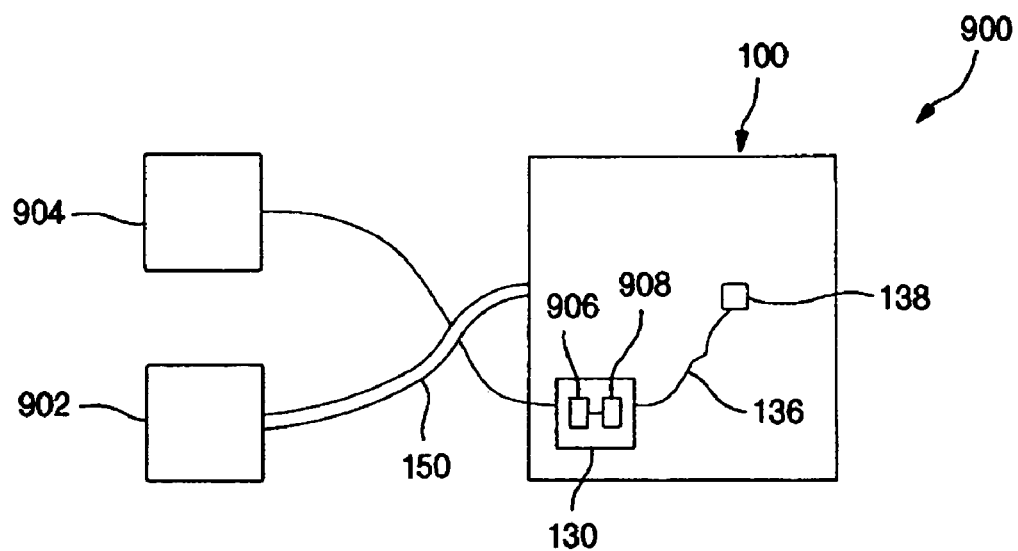
FIG. 9 is a block diagram view of a control embodiment of the present invention.

FIG. 9 shows a block diagram of an embodiment 900 of an apparatus such as apparatus 100 and its connects to an external vacuum pump 902 and computer control 904. In one embodiment, motor 130 includes processor 906 and memory 908, whose functions have been described above.

Figure 11:
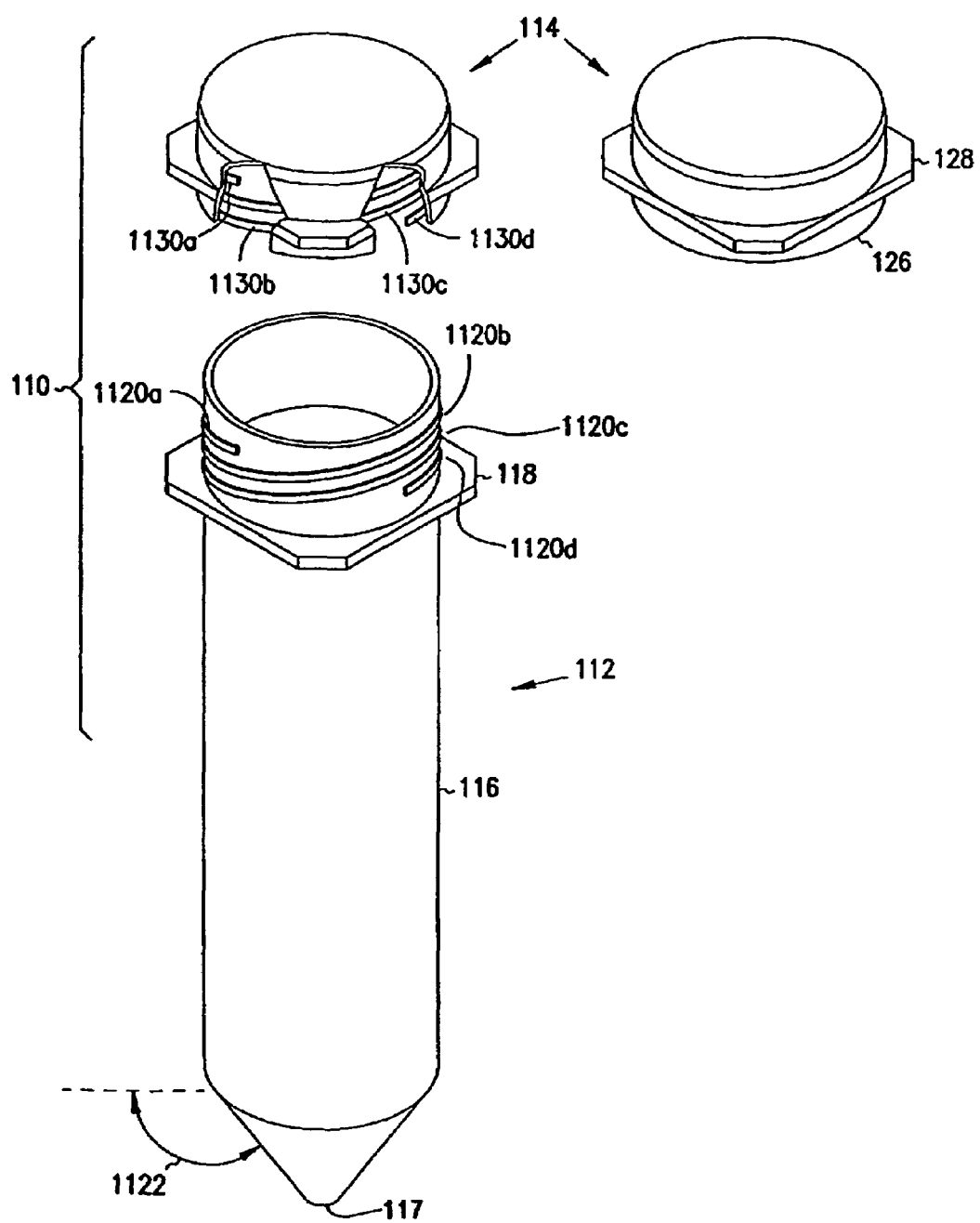
FIG. 11 is an exploded perspective view of a cap and vessel in one embodiment of the present invention.

One embodiment of the cap and vessel assembly 110 is shown in FIG. 11. In this embodiment, the cap and vessel assembly 110 comprises a vessel 112 and a cap 114. The vessel 112 comprises a vessel body (or skirt) 116 contiguous with a vessel flange 118. The vessel body 116 has individual or "disjointed" external threads 1120a, 1120b, 1120c and 1120d (hereinafter "1120a-1120d") visible on one side of an upper portion of the vessel body 116 above the vessel flange 118. There can be any suitable distance or "groove" between the external threads 1120a-1120d. In one embodiment, the distance between threads is about two to three times the thickness of each thread.

The vessel body 116 can be any size and shape depending on the application. It should be understood that for different sizes and shapes of vessels, different locking openings and ports are contemplated, and are within the scope of the invention. In one embodiment, the vessel body 116 is a cylindrically-shaped tube as shown in FIG. 11. Such a tube can have a tapered bottom as shown in FIG. 11, or can have a flat or rounded bottom as desired. This type of tube is typically used in a laboratory as a test tube into which small amounts of samples and reagents are placed.

In one embodiment, the vessel 112 is a tube that holds about 50 ml of fluid material and has a length of about 11.4 cm (about 4.5 in), an inner diameter of about 2.8 to three (3) cm (about 1.1 to 1.2 in) with a wall thickness of about 0.1 cm (about 0.4 in). The tapered bottom can be designed in any suitable manner. In one embodiment, the tapered portion has an angle 1122 of about 54 degrees starting about 1.5 cm (about 0.6 in) up from the bottom in a vessel 112 having an overall length of about 11.4 cm.

The disjointed external threads 1120a-1120d, can have any known type of profile or form, such as American Standard, square, Acme, and so forth. In another embodiment, conventional joined single or multiple threads are used. In the embodiment shown in FIG. 11, quadruple or "four-start" external disjointed threads are used. In this way the cap 114 can be securely fastened to the vessel 112 with a minimum of turning. The threads can be present along any suitable length of the vessel 112 and in one embodiment, extend to just above the vessel flange 118. In one embodiment, the external threads 1120a-1120d cover about the upper 1.2 cm (0.48 in) of a vessel having an overall length of about 11.4 cm.

In a disjointed thread configuration, each individual thread typically extends around the circumference of a vessel body in proportion to the number of disjoint threads in the configuration. In a triple or "three-start" configuration, there are three separate threads, each of which start and stop at approximately 120 degree intervals. In a "four-start" thread configuration, as shown in FIG. 11, there are four separate external threads 1120a-1120d. Each external thread 1120a-1120d starts and stops at approximately 90 degree intervals in relation to the adjacent thread, and each thread extends approximately 180 degrees around the top of the vessel body 116.

Figure 11A:
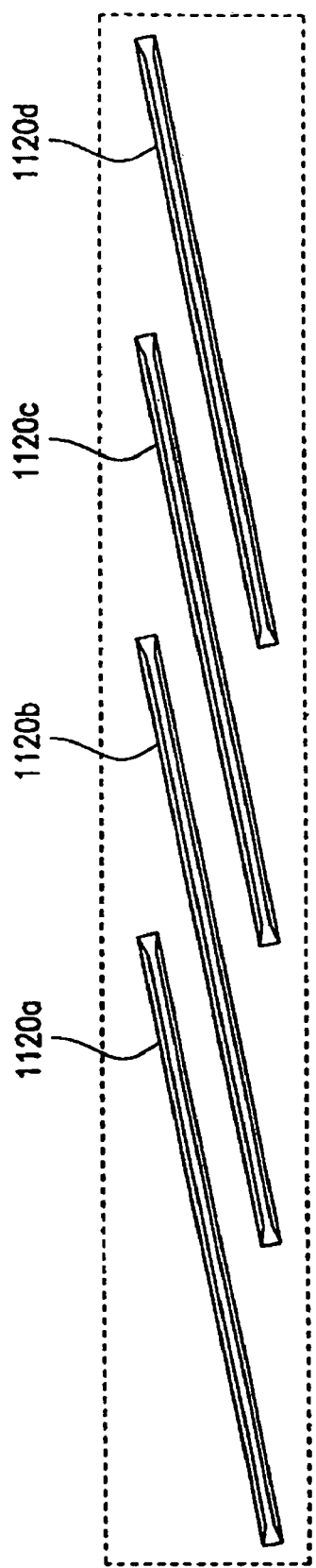
FIG. 11A is a roll-out view of multiple disjointed threads in one embodiment of the present invention.

In a roll-out view of the external threads 1120a-1120d shown in FIG. 11A, it can be seen that each thread starts at the about the same distance down from the top of the vessel body 116. As such, a corresponding cap with four matching disjointed threads (which have the same configuration as shown in FIG. 11A) will initially rest on all four external threads 1120a-1120d on the vessel body 116 no matter where it is placed on the vessel 112.

In the embodiment shown in FIGS. 11 and 11A, the threads are male threads that are all at a slight angle in relation to horizontal, although the invention is not so limited. Angling the threads in this way, however, allows them to be molded more easily. Further, the slight angle provides an upwardly facing relief face on the lower side of the external threads 1120a-1120d as is known in the art. In one embodiment, the angle is about ten (10) to 25 degrees. In another embodiment, the angle is about 20 to 22 degrees.

Referring again to FIG. 11, the vessel flange 118 can be any suitable size and shape provided it can serve to hold the vessel 112 in a fixed position on a suitable locking arm, such as the locking arm 106 or supplemental cradle 107 of mixing and pouring device 100 discussed above. In one embodiment, the vessel flange 118 is compatible with the corresponding cap flange 128 discussed in more detail below. In one embodiment, the vessel flange 118 is substantially square, triangular, round or rectangular shaped. In the embodiment shown in FIG. 11, the vessel flange 118 is substantially square shaped with each corner is angled, although the invention is not so limited. However, by removing the sharp edges at each corner, added comfort is provided for the person handling the vessels 112 and caps 114.

In one embodiment, the vessel flange 118 surrounds the entire circumference of the vessel body 116. The vessel flange 118 can be any suitable size in relation to the vessel body 116. In one embodiment, the combined diameter of the vessel body 116 and vessel flange 118 is about one (1) to 15% greater than the outer diameter of the vessel body 116 along all sides. In another embodiment, the vessel flange 118 extends beyond the vessel body 116 only in the corner areas of the vessel flange 118. In another embodiment, the vessel flange 118 does not surround the entire circumference of the vessel body 116, and is present only on certain portions of the vessel body 116, such as on two opposing sides or at three or more locations, such as in a spoke arrangement. In one embodiment, the vessel flange is about 0.02 to 0.6 cm (about 0.008 to 0.24 in) thick.

The cap 114 comprises a cap body (or skirt) 126 and cap flange 128, which is integral with the cap body 126. The cap body 126 shown in FIG. 11 is substantially circular in shape and has a circular internal ridge (shown in FIG. 12B) around which the top of the vessel body 116 sets. The cap body 126 further has internal threads 1130a, 1130b, 1130c and 1130d (hereinafter "1130a-1130d") as shown. The internal threads 1130a-1130d can be any conventional type of threads, but in one embodiment are also individual or disjointed threads substantially identical to the external threads 1120a-1120d on the vessel body 116. In one embodiment, the internal threads 1130a-1130d are also male threads. In another embodiment, the internal threads 1130a-1130d are female threads. Molding female threads in this manner is more difficult, however, because the cap body 126 needs to be thickened to compensate for loss of wall thickness in the area of the threads. The end result is a larger and thicker cap 114.

The internal threads 1130a-1130d can be substantially horizontal or at any suitable relief angle, which can be a minimum relief angle as shown in FIG. 11. As noted above, angling the internal threads 1130a-1130d in this manner allows them to be molded more easily as discussed above, although the angle should not be so steep as to cause the internal threads 1130a-1130d to "jump" the external threads 1120a-1120d on the vessel body 116 when being screwed on. Further, angling the threads in this manner provides a downwardly facing pressure face on the upper side of the internal threads 1130a-1130d as is known in the art. In one embodiment, the angle is about ten (10) to 25 degrees. In another embodiment, the angle is about 20 to 22 degrees.

The dimensions and shape of the cap flange 128 are substantially identical to the corresponding vessel flange 118. In one embodiment, the cap flange 120 is substantially square and is nearly flush with the outer diameter of the cap body 126 on four sides, extending outwardly from the cap body 126 only in the four corner areas as shown in FIG. 11.

The vessel 112 and cap 114 can be made from any suitable material. In one embodiment, the vessel 112 and cap 114 are made from an inert material which does not react with the contents of the vessel. In a particular embodiment, the vessel 112 and cap 114 are injection molded with polypropylene. Each component further has a small draft in order to remove the die as is known in the art. Additionally, the parting line flash for each can be held to any suitable amount, such as less than about 0.003 in witness, as is known in the art.

In one embodiment, the male threads in both the cap and vessel are made with an unscrewing core or die which leaves strong and substantial threads to provide a tight lock-up with mating threads. This is in contrast to internal cap threads made using a steel core pin, which are typically very rounded so the cap can be easily snapped off the molding core pin. In one embodiment, the threading cores in the die for the caps and vessels have virtually identical phasing relationships such that the internal (cap) threads 1130a-1130d produced in the die are virtually identical and in phase with the external (vessel) threads 1120a-1120d, all of which are also virtually identical. Further, by molding in virtually identical anti-rotating devices, i.e., vessel flanges 118 and cap flanges 128, on both the vessel 112 and cap 114 at the same point in relation to the threads, all of the internal threads 1130a-1130d in every cap 114 locate virtually to the same depth as every other cap 114.

The cap body 126 and vessel body 116 can further have any suitable texture. In one embodiment, some or all of the cap body 126 and/or vessel body 116 has a knurled or ridged texture comprised of a series of vertical lines. Typically such a knurled surface aids in gripping and serves as a type of "anti-rotation" device. This type of surface may be useful in embodiments in which there are no other anti-rotation devices, i.e., the cap flange 128 and/or vessel flange 118.

In operation, the cap body 126 is placed over the vessel body 116 and the cap 114 can be given a turn sufficient to provide sealing of the contents inside the vessel 112. With a four-start thread configuration for the external threads of the vessel 112 as described above, it is possible to obtain an adequate seal with less than a ¼ or 90 degree turn of the cap body 126 in relation to the vessel body 116. In another embodiment, the cap body 126 is turned any amount up to 360 degrees. The amount of rotation needed to secure the cap 114 depends on where the cap 114 is placed initially. In any of these embodiments, the vessel 112 is sealed when the edges of the flanges (118 and 128) are aligned. Specifically, in one embodiment, the cap 114 comes to an abrupt stop at this point and further turning does nothing to change the relationship between the cap 114 and vessel 112. This is due to the particular design of the internal and external threads 1130a-1130d and 1120a-1120d, respectively, including the profile shape, angle, and so forth. The amount of rotation required to remove the cap 114 from the vessel 112 can be designed to be any suitable amount. In one embodiment, the assembly 110 is designed to require a 180 degree rotation for removal. Such rotation amount depends on the ramp angle of the threads, space between the top of cap 114 and beginning of the threads, and so forth. In this way, a suitably designed automated device, such as a cap rotator, discussed below, can be used to secure and remove the caps 114 by rotating the cap (114) 180 degrees in either direction. In this embodiment, the assembly 110 can be designed to require up to a 180 degree rotation for removal even if less than a 180 degree rotation is needed to secure the cap 114 to the vessel 112. In one exemplary embodiment, the ramp angle of the internal threads 1130a-1130d is about 21 degrees and the threads are spaced down about 0.44 cm (0.175 in) from the top of a cap 114 having an inner diameter of about 2.7 cm (1.05 in) and an outer diameter of about 2.8 cm (1.12 in).

With use of multiple individual threads, the internal threads 1130a-1130d of the cap 114 load on multiple and separate thread surfaces (1120a-1120d) on the vessel body 116, rather than on only one, providing a more stable positioning system. Although multiple threads provide enhanced stability as compared with a single thread, some tipping can still occur with double and triple thread configurations. With use of the four-start threads for the external threads of the vessel body 116, there are four individual threads 1120a-1120d onto which the four internal threads 1130a-1130d of the cap 114 are in communication with initially as shown above in FIG. 11A, providing a flat plane, thus preventing tipping. In this way, the cap 114 can be taken on and off relatively quickly.

Additionally, use of the cap flange 128 not only helps with correctly positioning and repositioning the cap body 126 on the vessel body 116, it also serves as a strengthening device. Specifically, with the cap flange 128 present, the cap body 126 can not expand or bend if excess torque is applied. Similarly, the vessel flange 118 prevents the vessel body 116 from caving in if the cap body 126 is secured to the external threads 1120a-1120d with excess torque. Generally, the use of torque is not required with this type of thread arrangement, and complete sealing can be obtained with minimal turning, as noted above.

Figure 12A:
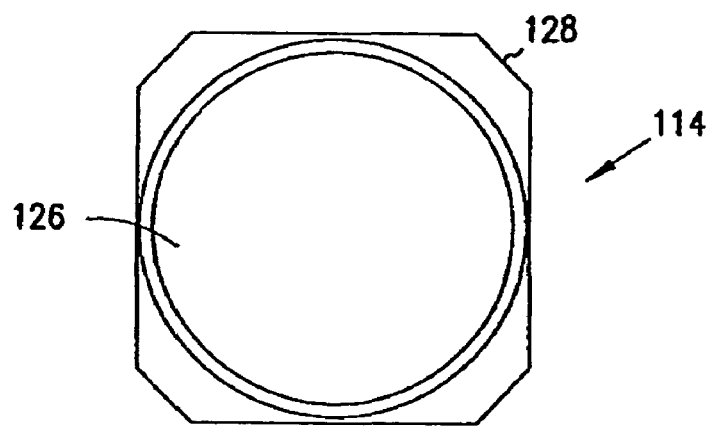
FIG. 12A is a top view of a cap in one embodiment of the present invention.
Figure 12B:
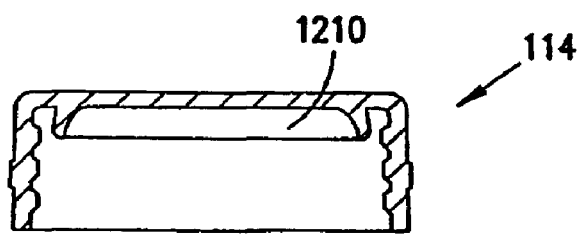
FIG. 12B is a cross-sectional view of a cap in one embodiment of the present invention.
Figure 12C:
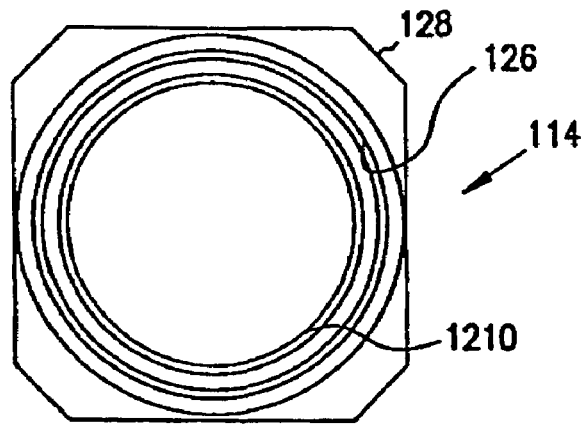
FIG. 12C is a bottom view of a cap in one embodiment of the present invention.

FIG. 12A is a top view of the cap 114, showing the cap flange 128 and cap body 126 as described above. FIG. 12B is a cross-sectional view of the cap 114 showing the cap body 126 and internal threads 130. As noted above there is also an internal ridge 1210 around which the top of the vessel body fits. FIG. 12C is a bottom view of the cap 114 showing the cap flange 128, as well as the inner and outer diameters of the cap body 126 and the internal ridge 1210.

Figure 13A:
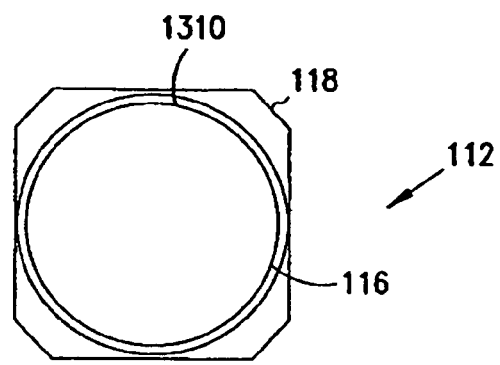
FIG. 13A is a top view of a vessel in one embodiment of the present invention.
Figure 13B:
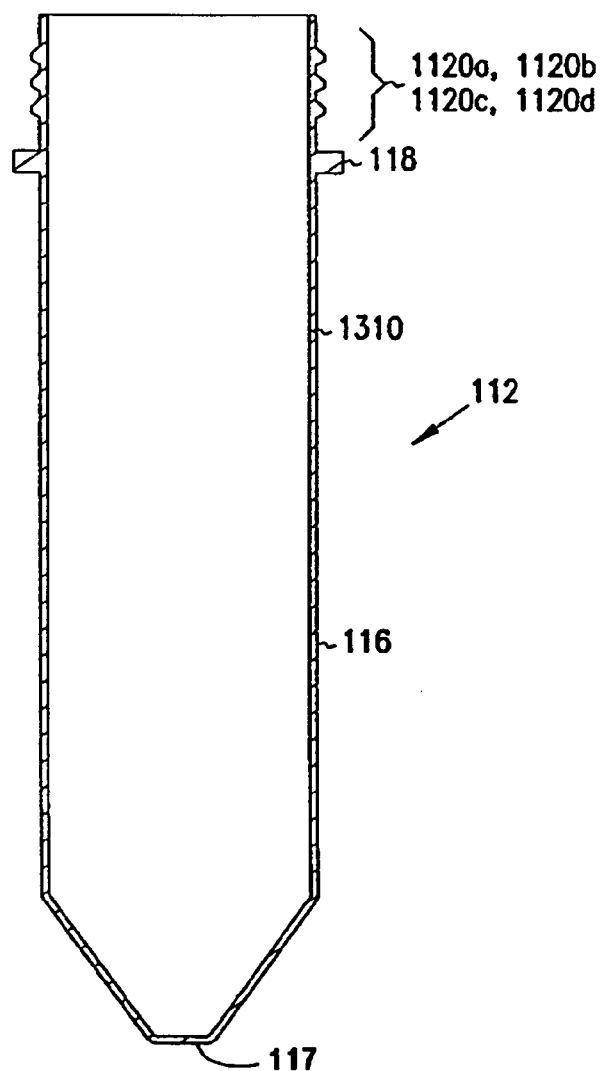
FIG. 13B is a cross-sectional view of a vessel in one embodiment of the present invention.

FIG. 13A is a top view of the vessel 112 showing the vessel flange 118 and vessel body 116. The wall 1310 of the vessel body 116 can also be seen in this view. FIG. 13B is a cross-section of the vessel 112 showing the wall 1310, the vessel flange 118 and the external threads 1120a-1120d as described above.

Figure 14:
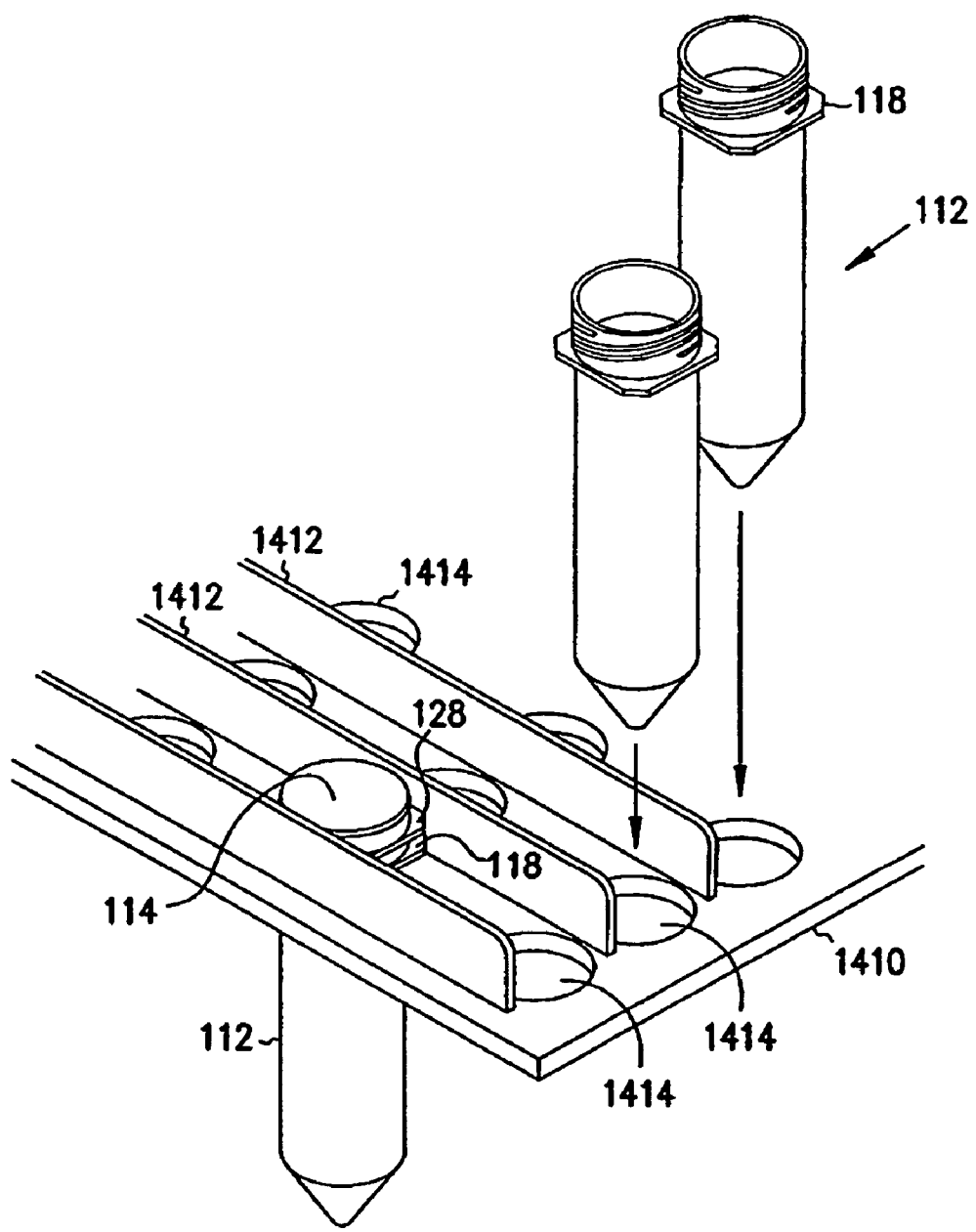
FIG. 14 is a cut-away perspective view of vessels in place on a lab rack in one embodiment of the present invention.

The assembly 110 can be placed in any number of devices that serve to hold the assembly 110 in position and further aid in positioning the cap 114 to the vessel 112. FIG. 14 shows one embodiment of a lab rack 1410 which has been modified to have partitions 1412 between rows of holes 1414. Any suitably sized lab rack 1410 can be used. In one embodiment, there are four rows of holes 1414, each row having eight (8) holes 1414 through which 32 vessels 112 can be placed. In this embodiment, the partitions 1412 run the entire length of the lab rack 1410. The partitions 1412 are spaced such that two opposing sides of each vessel flange 118 are in contact with adjacent partitions 1412 when in place on the rack 1410 and properly positioned. In this way, the vessel 112 is held securely in place so that samples or reagents can be added, the vessel 112 can be capped, and so forth.

In one embodiment, a lab operator loads a portion of the rack 1410, such as about half, with samples. If a bar code is present on the vessel 112, that can be scanned into a suitable scanning device at this time. When the operator is ready to seal the contents of a vessel 112, the operator manually places a cap 114 (which can also have a bar code) onto a vessel 112, turning the cap 114 until the cap flange 126 is aligned with the vessel flange 118. As with the placement of the vessels 112, the presence of the partitions 1412 on either side of each row insures that the caps 114 will be placed in the correct position. Specifically, if the vessel flanges 118 and cap flanges 128 are not in alignment, the vessels 112 and caps 114 will not fit in between the partitions 1412. Further, as discussed above, the thread design and seating tolerances cause the cap 114 to come to an abrupt stop when it is in proper alignment, so that this proper alignment is easily achieved. Therefore, with substantially square cap and vessel flanges, 128 and 118, respectively, the cap 114 and vessel 112 can be dropped into position in four different ways, i.e., along any of the four edges of the flanges 118 and 128.

Figure 15:
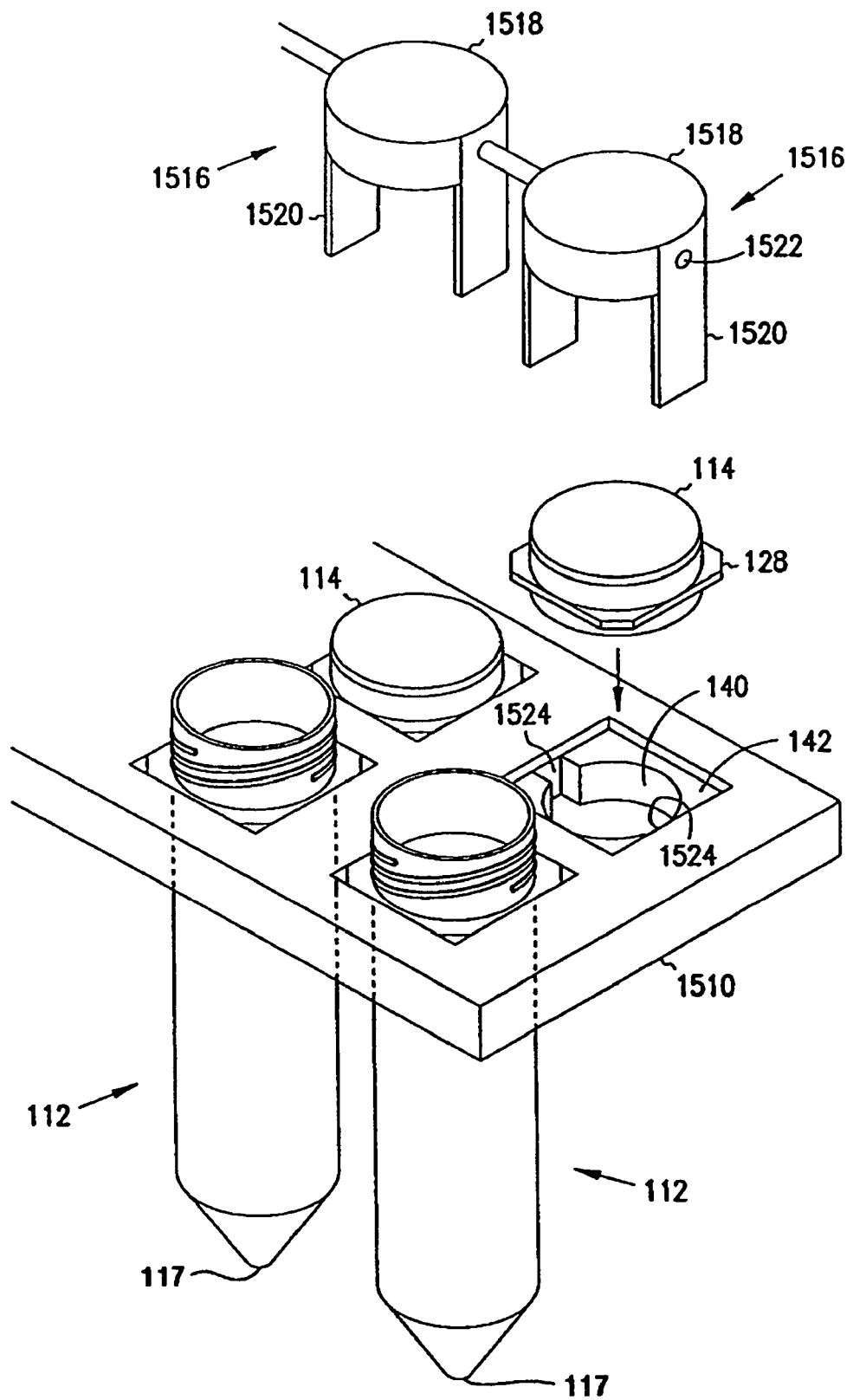
FIG. 15 is a cut-away perspective view of vessels and caps in a storage rack in one embodiment of the present invention.

FIG. 15 shows a shuttle device 1510 which is used to store the cap 114 and vessel 116. The cap 114 and vessel 112 can be stored in the shuttle device 1510 when not in use, or for transport during any type of procedure. Such procedure can be any type of manual or automated procedure. As FIG. 15 shows, the shuttle device 1510 contains pairs of identical holes for storing a vessel 112 and its corresponding cap 114. The shuttle device 1510 comprises the same type of holes 140, each with a step or locking pocket 142 as the mixing and pouring device 100 discussed in FIG. 1. The locking pocket 142 is designed to be the same size and depth as the flanges, i.e., cap flange 128 and vessel flange 118. The shuttle device 1510 can contain any number of holes 140 as desired for a particular application. In one embodiment, there are four (4) pairs of holes 140 to support four pairs of vessels and caps.

When capping the vessel 112, the cap 114 can be picked up, placed on the vessel 112 and rotated the desired amount, such as 90, 180, 270 or 360 degrees. In one embodiment, the cap 114 is rotated approximately 180 degrees clockwise in relation to the vessel 112. When the cap 114 is removed from the vessel 112, it is rotated the same amount in reverse and placed back in its original hole. In one embodiment, the cap 114 is screwed onto the vessel 112 with a ½ or 180 degree rotation in one direction and unscrewed with a ½ or 180 degree rotation in the opposite direction.

In one embodiment, the caps 114 are picked up simultaneously and automatically by a series of cap rotators 1516, placed on the vessel 116 and rotated 180 degrees. Each cap rotator 1516 comprises a cap rotator body 1518 and two blades or fingers 1520. The blades 1520 can be made from any suitable material, such as replaceable tool steel. In one embodiment, the blades 1520 are secured to the rotator cap body 1518 with a suitable connector 1522. Each cap rotator 1516 further has an internal suction cup (not shown) to hold the cap 114 firmly in place as it is being transported or rotated. Any number of cap rotators 1516 can be used so that multiple caps 114 can be picked up and moved simultaneously.

Figure 10:
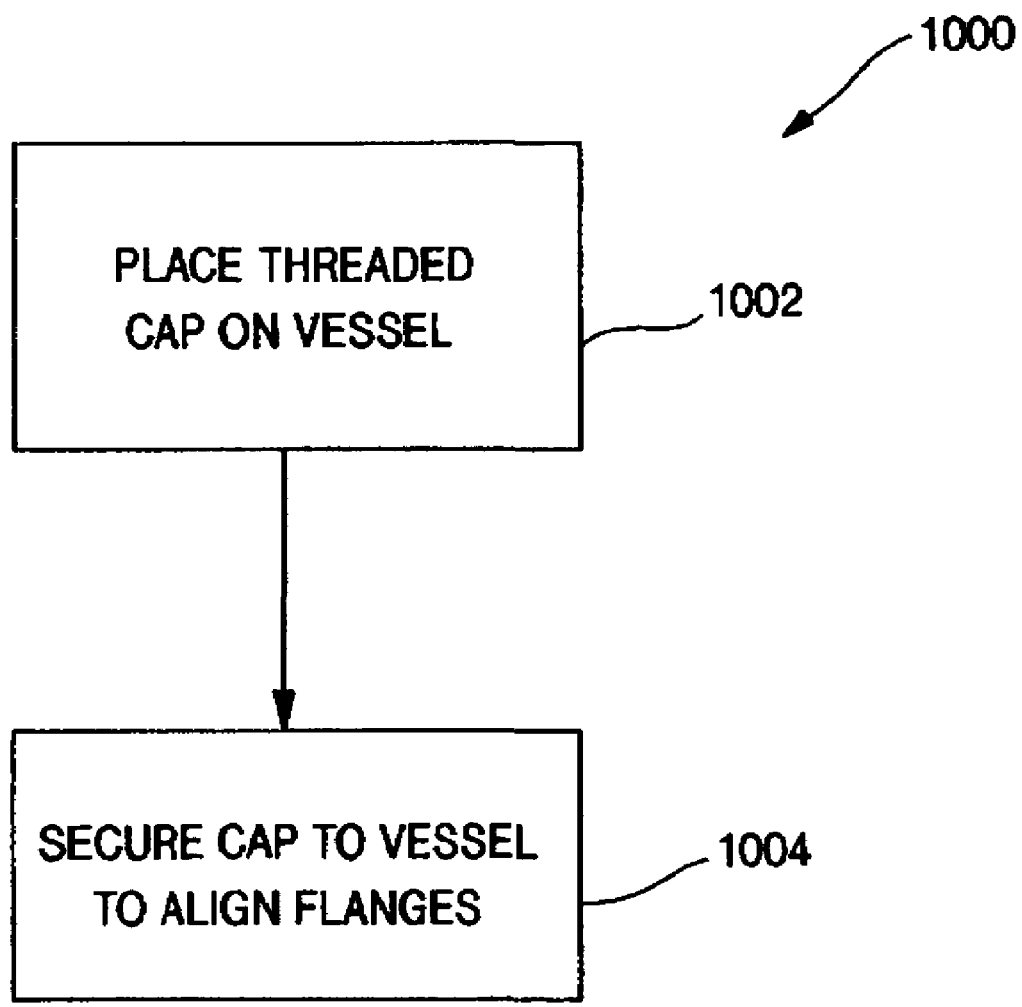
FIG. 10 is a flow chart diagram of a method embodiment of the present invention.

An embodiment of the vessel sealing method 1000 described herein is shown in FIG. 10. Method 1000 comprises placing a threaded cap having a cap flange on a threaded vessel having a vessel flange in block 1002, and securing the threaded cap to the threaded vessel a first time by rotating the threaded cap in one direction, the threaded cap secured to the threaded vessel when the cap flange and vessel flange are aligned in block 1004.

In the embodiment shown in FIG. 15, each of the holes 140 further have recesses 1524 on opposing sides into which the opposing blades 1520 on the cap rotator 516 slide to pick up the cap 114 in order to move it out of the locking pocket 142. The process is completed in reverse when it is desired to remove the cap 114. In other words, the cap 114 is rotated 180 degrees in the reverse direction and returned to the locking pocket 142 in the same position it began. The screwing and unscrewing of the cap 114 and placement in the locking pocket 142 can also be completed manually. In one embodiment, bar codes are used to identify the vessel 112 and cap 114 so that the same cap 114 is always used with the same vessel 112. This helps to ensure that there is no contamination or cross-contamination, although in most embodiments all of the vessels 112 and caps 114 are made with the same die so that the caps and vessels are interchangeable.

The shuttle device 1510 or the cap rotators 1520 can also be used to move the vessels 112 and caps 114 to any location desired in the process, such as underneath reagent dispensing devices, to centrifuging stations and into alignment with subsequent lab racks 1410 (shown in FIG. 14).

The shuttle device 1510 can also transport vessel and cap assemblies 110 to the mixing and pouring station 100 described above, as shown in FIG. 16. The holes 140 with opposing recesses 1524 as well as the locking pocket 142 are the same as shown in previous figures. By locking the flanges, 128 and 118, in place in this way, the assembly 110 does not come loose and start to reposition itself during a shaking or pouring step. Any suitable number of assemblies 110 can be placed in the mixing and pouring station 100. In one embodiment, eight assemblies 110 are placed in this device. The assemblies 110 can be moved to this location manually or automatically, such as with the cap rotator 1516 as shown. In the embodiment shown in FIG. 16, the vacuum port 144 serves to further secure the vessel 116 in place, particularly when the cap 114 is being rotated on or off.

The various holding devices shown in FIGS. 1, 14, 15 and 16 can be used individually or in combination in any type of automated or manual laboratory or manufacturing procedure as described above.

The mixing and pouring apparatus 100 allows a user to more closely control the operations of mixing, agitating, and pouring. The apparatus 100 is precisely controlled by the motor 130 and external computer control, so that it is capable of performing any number of programmed tasks.

Furthermore, the cap and vessel flanges of the present invention provide means to cap and recap a vessel without losing track of where threads are located on the vessel, such that the cap is resecured to the vessel in substantially the identical location and manner each and every time. Rotation of the cap then engages the two sets of threads evenly and consistently. Once the flanges are oriented in the same direction, the vessel is tightly sealed. Proper alignment also ensures that the vessel is locked into position for transport, shaking, and so forth. Through use of multiple disjointed threads on the vessel, the cap and vessel positioning system of the present invention has the added advantage of providing a tight seal with only a minimum amount of turning.

The program that is executed by a computer issues output in the form of commands for controlling the operation of an automated machine for performing the centrifuging, aspirating, dispensing, and mixing operations. Program modules within the program allow for the custom control of the four basic processes, centrifugation, aspiration, mixing, and dispensing, of DNA isolation.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the invention. It is intended that this invention be limited only by the following claims, and the full scope of equivalents thereof.

What is claimed is:

1. A computer system for configuring a machine to automatically perform a method of isolating nucleic acid, the computer system comprising:
   a computer;
   a computer readable medium comprising machine readable instructions for causing the computer to output a command series to an automated nucleic acid isolation machine for control of the functions of nucleic acid isolation process;
   wherein the computer readable medium further comprises:
   a software module comprising:
      a centrifuge sub-module for issuing commands initiating centrifuging of a sample for a centrifuge time and a centrifuge speed;
      an aspirate sub-module for issuing commands initiating aspirating a sample to remove a volume of fluid from a sample;
      a mixing sub-module for issuing commands initiating mixing a sample; and
      a dispensing sub-module for issuing commands initiating dispensing into a sample an amount of a specific reagent; wherein the command series comprises:
   loading a vessel containing a biological blood sample into a centrifuge;
   centrifuging the sample for a predetermined time and at a predetermined g-force;
   removing excess supernatant from the centrifuged sample;
   mixing the biological blood sample in the vessel by aspirating and dispensing a predetermined quantity of sample a predetermined number of times;
   dispensing into the biological blood sample a predetermined quantity of a first reagent;
   mixing the biological blood sample in the vessel by aspirating and dispensing a predetermined quantity of sample a predetermined number of times;
   dispensing into the sample a predetermined quantity of a second reagent;
   mixing the sample by aspirating and dispensing a predetermined quantity of sample a predetermined number of times;
   centrifuging the sample for a predetermined time and at a predetermined g-force;
   removing excess supernatant from the sample;
   transferring material remaining after removing excess supernatant to a second vessel containing a predetermined volume;
   mixing the sample by aspirating and dispensing a predetermined quantity of sample at a selectable aspiration rate from gentle to vigorous a predetermined number of times;
   centrifuging the sample for a predetermined time and at a predetermined g-force;
   removing excess supernatant from the sample;
   dispensing into the sample a predetermined quantity of a third reagent;
   mixing the sample by aspirating and dispensing a predetermined quantity of sample at a selectable aspiration rate from gentle to vigorous a predetermined number of times;
   centrifuging the sample for a predetermined time and at a predetermined g-force;
   removing a predetermined quantity of material from the sample; and
   dispensing into the sample a predetermined amount of a fourth reagent.

2. The computer system of claim 1, wherein the command series further comprises removing and storing the vessel containing the biological blood sample.

3. The computer system of claim 1, wherein the command series further comprises dispensing additional reagents as necessary.

4. The computer system of claim 1, wherein the computer readable medium comprises:
   a control module comprising:
      a program module comprising a set of machine readable instructions for issuing commands to the automated nucleic acid isolation apparatus to perform a series of steps on the sample, comprising:
         centrifuging the sample;
         removing the sample;
         mixing the sample; and
         adding a reagent to the sample.

5. The computer system of claim 4, wherein the control module is implemented in a dedicated processor.

6. The computer system of claim 4, wherein the program module is burned into a processor in hard code.

7. The computer system of claim 4, wherein the program module is implemented in a programmable logic controller.

8. A computer system for configuring a machine to automatically perform a method of isolating nucleic acid, the computer system comprising:
   a computer;
   a computer readable medium comprising machine readable instructions for causing the computer to output a command series to an automated nucleic acid isolation machine for control of the functions of nucleic acid isolation process;
   wherein the computer readable medium further comprises:
   a software module comprising:
      a centrifuge sub-module for issuing commands initiating centrifuging of a sample for a centrifuge time and a centrifuge speed;
      a removal sub-module for issuing commands initiating removing from a sample container volume of fluid from the sample;
      a mixing sub-module for issuing commands initiating mixing the sample; and a dispensing sub-module for issuing commands initiating dispensing into the sample an amount of a specific reagent;

wherein each sub-module except the centrifugation sub-module is configured to control operation external to a centrifuge.

9. The computer system of claim 8, and further comprising:

a graphical user interface for selecting a sequence of commands to be output by the computer.

10. The computer system of claim 8, wherein the computer readable medium comprises:

a control module comprising:

a program module comprising a set of machine readable instructions for issuing commands to the automated nucleic acid isolation apparatus to perform a series of steps on a sample, comprising:

centrifuging the sample;
removing the sample;
mixing the sample; and
adding a reagent to the sample.

11. The computer system of claim 8, wherein the computer readable medium comprises a control module, the control module comprising:

a plurality of sub-modules, each sub-module comprising machine readable instructions for creating a command to the nucleic acid isolation apparatus to perform a process step of the nucleic acid isolation process; and an output link for communicating the commands to the nucleic acid isolation apparatus.

12. The computer system of claim 11, wherein the plurality of sub-modules comprises:

a centrifuge sub-module for issuing commands initiating centrifuging of the sample for a predetermined time and speed;

a removal sub-module for issuing commands initiating removing a volume of fluid from the sample;

a mixing sub-module for issuing commands initiating mixing the sample; and a dispensing sub-module for issuing commands initiating dispensing into the sample an amount of a specific reagent.

13. The computer system of claim 11, and further comprising a user input/output interface for programming a process comprising a plurality of invocations of the various sub-modules of the computer module.

14. The computer system of claim 11, wherein each of the sub-modules is configured to accept input of values for issuing commands.

15. The computer system of claim 8, wherein the command series comprises:

dispensing into a sample in a first vessel a predetermined quantity of a first reagent;
mixing the sample;
centrifuging the sample;
removing excess supernatant from the centrifuged sample;
dispensing a predetermined quantity of a second reagent into the sample;
dispensing a predetermined quantity of a third reagent into the sample;
mixing the sample;
centrifuging the sample;
transferring a supernatant fraction of the sample containing nucleic acid to a second vessel;
dispensing a fourth reagent into the fraction of the sample;
mixing the fraction of the sample;
centrifuging the fraction of the sample;
dispensing a fifth reagent to the fraction of the sample;
mixing the fraction of the sample;
centrifuging the fraction of the sample;
dispensing a sixth reagent into the fraction of the sample;
mixing the fraction of the sample; and
centrifuging the fraction of the sample.

16. The computer system of claim 15, wherein mixing comprises rotating a predetermined number of times at a predetermined rate.

17. The computer system of claim 15, wherein centrifuging comprises:

loading the vessel containing a sample into a centrifuge;
centrifuging the sample for a predetermined time and speed; and
unloading the vessel containing a biological sample after centrifugation.

18. A computer system for configuring a machine to automatically perform a method of isolating nucleic acids, the computer system comprising:

a computer;

a computer readable medium comprising machine readable instructions for causing the computer to output a command series to an automated nucleic acid isolation machine for control of the functions of nucleic acids isolation process;

wherein the computer readable medium comprises:

a software module comprising:

a centrifugation sub-module for issuing commands initiating centrifuging of a sample for a centrifuge time and a centrifuge speed;

a mixing sub-module for issuing commands initiating mixing a sample;

a dispensing module for issuing commands initiating dispensing into a sample an amount of a specific reagent;

a temperature control module for issuing commands to control the temperature of a function;

a removal module for issuing commands to remove material from a sample;

a separation module for issuing commands to separate a sample into components; and a combination removal and separation module for issuing commands to control separating and removing a sample;

wherein each sub-module except the centrifugation sub-module is configured to control operation external to a centrifuge.

19. The computer system of claim 18, and further comprising:

a graphical user interface for selecting a sequence of commands to be output by the computer.

20. A computer control module for an automated nucleic acids isolation apparatus, the control module comprising:

a plurality of sub-modules, each sub-module comprising machine readable instructions for creating a command to the nucleic acids isolation apparatus to perform a process step of the nucleic acids isolation process; and an output link for communicating the commands to the nucleic acids isolation apparatus;

wherein the plurality of sub-modules comprises:

a centrifuge sub-module for issuing commands initiating centrifuging of a sample for a centrifuge time and a centrifuge speed;

a mixing sub-module for issuing commands initiating mixing a sample;

a dispensing module for issuing commands initiating dispensing into a sample an amount of a specific reagent;

a temperature control module for issuing commands to control the temperature of a function;

a removal module for issuing commands to remove material from a sample;

a separation module for issuing commands to separate a sample into components; and a combination removal and separation module for issuing commands to control separating and removing a sample;

wherein each sub-module except the centrifugation sub-module is configured to control operation external to a centrifuge.

21. The computer module of claim 20, and further comprising a user input/output interface for programming a process comprising a plurality of invocations of the various sub-modules of the computer module.

22. The computer module of claim 20, wherein each of the sub-modules is configured to accept input of values for issuing commands.

23. The computer control module of claim 22, wherein the control module is implemented in a machine readable medium comprising a set of machine readable instructions.

24. The computer module of claim 20, wherein the control module is implemented in a dedicated processor.

25. A computer system for configuring a machine to automatically perform a method of isolating nucleic acids, the computer system comprising:

a computer;

a computer readable medium comprising machine readable instructions for causing the computer to output a command series to an automated nucleic acid isolation machine for control of the functions of nucleic acids isolation process;

wherein the computer readable medium comprises:

a software module comprising:

a centrifugation sub-module for issuing commands initiating centrifuging of a sample for a centrifuge time and a centrifuge speed;

a mixing sub-module for issuing commands initiating mixing the sample;

a dispensing module for issuing commands initiating dispensing into the sample an amount of a specific reagent;

a temperature control module for issuing commands to control the temperature of a function;

a removal module for issuing commands to remove material from the sample;

a separation module for issuing commands to separate the sample into components; and a combination removal and separation module for issuing commands to control separating and removing the sample;

wherein each sub-module except the centrifugation sub-module is configured to control operation external to a centrifuge.

26. The computer system of claim 25, wherein the system operates on samples having a sample volume of approximately 10 milliliters.

27. The computer system of claim 25, wherein the system operates on samples having a sample volume of up to 50 milliliters.

* * * * *